United States Patent [19]

Lundquist

[11] 4,165,208

[45] Aug. 21, 1979

[54] INTRAVENOUS DELIVERY PUMP

[75] Inventor: Ingemar H. Lundquist, Oakland, Calif.

[73] Assignee: Valleylab, Boulder, Colo.

[21] Appl. No.: 860,789

[22] Filed: Dec. 15, 1977

Related U.S. Application Data

[63] Continuation of Ser. No. 704,540, Jul. 12, 1976, abandoned, which is a continuation of Ser. No. 431,753, Jan. 8, 1974, Pat. No. 3,874,826, which is a continuation-in-part of Ser. No. 329,425, Feb. 5, 1973, abandoned.

[51] Int. Cl.² .............................................. F04B 39/10
[52] U.S. Cl. .................................... 417/565; 74/18.2; 222/373; 222/380
[58] Field of Search ................... 74/18, 18.1, 18.2; 184/24; 417/211.5, 507, 536, 568, 565, 559, 127; 128/214 F, 273, 214 C, 235, 234, 218 P, 218 PA, DIG. 12; 222/319, 373, 380, 409; 92/168, 130 B, 94, 89, 90, 93

[56] References Cited

U.S. PATENT DOCUMENTS

| | | | |
|---|---|---|---|
| 957,347 | 5/1910 | Kennedy | 92/130 B |
| 1,476,946 | 12/1923 | Bessesen | 128/218 P |
| 2,076,732 | 4/1937 | Kuehne | 417/536 |
| 2,244,483 | 6/1941 | Bayne | 137/527 |
| 2,342,906 | 2/1944 | Smith | 92/99 X |
| 2,572,952 | 10/1951 | Rymol | 184/24 |
| 2,608,207 | 8/1952 | LeVan | 74/18 |
| 2,664,829 | 1/1954 | Horton et al. | 222/373 |
| 2,734,667 | 2/1956 | Conklin | 222/380 |
| 3,159,317 | 12/1964 | Mini | 222/409 X |
| 3,559,644 | 2/1971 | Stoft et al. | 128/214 F |
| 3,798,982 | 3/1974 | Lundquist | 92/13.7 |
| 3,874,826 | 4/1975 | Lundquist | 417/565 |

FOREIGN PATENT DOCUMENTS 612148 1/1961 Canada ..................................... 417/437

*Primary Examiner*—Carlton R. Croyle
*Assistant Examiner*—Edward Look
*Attorney, Agent, or Firm*—Flehr, Hohbach, Test, Albritton & Herbert

[57] ABSTRACT

The present invention comprises a small, precise measuring pump provided with a germ barrier that is specifically designed for intravenous feeding devices and comprises: inlet and outlet chambers which are preferably integral one with the other, an inlet adapted to receive a tube from a storage device and the outlet chamber provided with an outlet adapted to receive a tube for delivery of material pumped to a patient; a passageway between the two chambers, which serves as an outlet from the inlet chamber and an inlet into the outlet chamber; a valve (preferably a float valve) associated with each inlet; and an actuating device which includes a piston and a tightly fitting resilient sheath enclosing the piston, the combination of piston and sheath projecting into the inlet chamber. The movement of the piston inwardly and outwardly within the inlet chamber provides the pumping force for the operation of the pump, and the sheath provides a sterile seal between the piston and the body of the pump and also, if made of resilient material, such as rubber, provides a force for returning the piston to an inoperative position. A pumping force may be applied to the external end of the piston by any suitable means.

23 Claims, 4 Drawing Figures

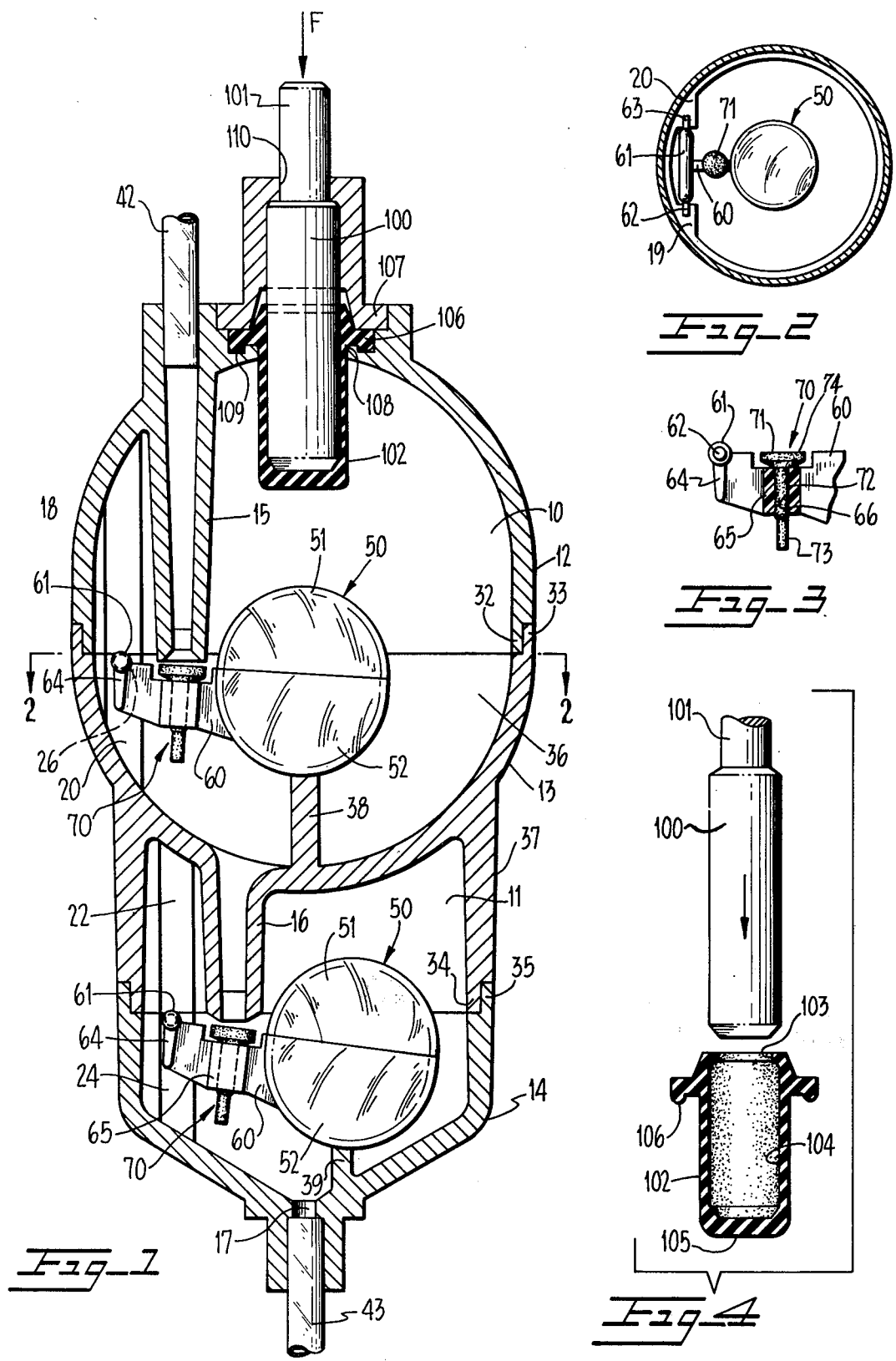

INTRAVENOUS DELIVERY PUMP

This application is a continuation of my application Ser. No. 704,540, now abandoned, which is a continuation of my application Ser. No. 431,753, filed Jan. 8, 1974 now U.S. Pat. No. 3,874,826, issued Apr. 1, 1975 which is a continuation-in-part of my application Ser. No. 329,425, filed Feb. 5, 1973 now abandoned.

BACKGROUND OF THE INVENTION

In recent years there has been considerable interest in intravenous delivery pumps, particularly for the feeding of saline solutions, and the like, to a patient. For many years such materials were fed to a patient only by the force of gravity, which necessitated placing the container containing the liquid for delivery to the patient at a considerable elevation above the patient. These devices were not entirely satisfactory in view of the height requirement and the difficulty in accurately regulating their flow. Regulation of flow could only be secured by counting drops of fluid in a predetermined period of time and then requiring periodical checking by a nurse. Furthermore, it was difficult to maintain a regulated flow over a prolonged period of time. Therefore, in recent years there has been a trend toward developing a positive acting pump which could be accurate in its delivery of intravenous feeding material to the patient, could be readily adjusted and would be positive in its operation, without requiring the placing of the bottle containing the liquid at some distance above the patient. The difficulty with these pumps has been, for the most part, that they were subject to slight variations in the quantity of material delivered, so that absolute accuracy was still impossible. They also have the disadvantage that they were rather expensive and could not be used once and then thrown away, and they were difficult to disassemble, sterilize, and re-assemble, so that sterilization and the maintenance of sterile conditions was difficult. One of the causes of inaccuracy in pumping was the shape of the chamber in which the pumping operation took place. If this is square or cylindrical in shape and is made of light plastic material, the exertion of a pumping force to the material within the chamber causes flexing of the chamber walls and therefore introduces inaccuracies. Many of these pumps used float valves, most of which were cylindrical in shape, and again the force applied to the liquid within the pumping chamber caused flexing of the top and bottom of the cylindrical float. Some of the pumps heretofore suggested have utilized a piston moving into and out of the pumping chamber to apply the pumping force to the liquid within the chamber and this introduced the possibility of leakage and, more important, the possibility of septic materials coming from outside the pump through the wall in which the piston operates and into the material in the chamber. Such a construction involved a rubbing contact between the piston and the wall of the pumping chamber, which produces wear and eventual leakage, and prevented their use for pumping blood.

These disadvantages have been removed in the present invention in which the pump is preferably made of light plastic material, so that it can be made in a few simple moldings and therefore is so inexpensive that it can be thrown away with each use. The pumping chamber is preferably spherical in shape so that the application of pressure to the liquid therein is equal in all directions and cannot deform spherical walls. I use, preferably, a particular form of float valve in which a spherical float is mounted on one end of a lever arm, the other end of which is pivoted to the walls of the respective chambers, which arm carries at an intermediate point a gasket aligned with the inlet into the respective chambers. The gasket preferably is located substantially closer to the pivot point than to the center of the spherical float, thereby giving the float increased force against the inlet due to the multiplication of force through the lever action. The pumping member is a piston enclosed in a tight fitting sheath which is preferably shaped to prevent the entrance of air between the sheath and the piston and is shaped so that the stretching of the sheath occurs in the cylindrical walls thereof rather than at the end, so that there is considerable force applied to the sheath against the piston to return it to its normal, inoperative position. Movement of the piston can be from any suitable prime mover, such as a small motor rocking a lever against the outer end of the piston. Further, the preferred form of pump shown and described permits it to be used as a positive acting and highly accurate pump when it is placed in one position, and can also be used in gravity feed by merely turning the pump upside-down. Thus, the device of the present invention can be used as a pump or in connection with gravity feed without removing it from the feed line, as conditions may warrant.

OBJECTS

It is a primary object of the present invention to provide a small pump particularly adapted for intravenous feeding, which is small in size, can be readily made of moldable materials, such as styrene, or other plastic, is inexpensive to fabricate, and which is extremely accurate in its rate of delivery.

It is another object of the present invention to provide an improved intravenous delivery pump in which there is no rubbing contact between the forcing element and any part of the pump casing, so that it can safely be used for pumping whole blood.

It is a further object of the invention to provide a very small, very light weight, and very precise measuring pump which has a germ barrier, that prevents the possibility of contamination of the material being pumped.

It is still another object of the present invention to provide a pump small in size and light in weight in which the rate of delivery can be readily adjusted by controlling the depth of movement of a piston into the pumping chamber and by the timing of the separate strokes.

It is another object of the present invention to provide an intravenous feeding device which cannot pump air into the patient's blood stream and which will become inoperative in the event a quantity of air becomes entrapped therein.

It is still another object of the present invention to provide a pump which can either be positively operated or used as a "flow-through" device by merely changing its position, so that it does not have to be removed from the supply system (with its consequent problems of maintaining sterile conditions) when it is desired to shift from positive operation to gravity feed.

These and other objects of the present invention will become apparent from a review of the accompanying drawings when taken in connection with the description which follows.

DRAWINGS

FIG. 1 is an enlarged cross-sectional side view of the pump of the present invention.

FIG. 2 is a cross-sectional plan view of the pump shown in FIG. 1 taken along the planes indicated by the lines 2—2 of FIG. 1.

FIG. 3 is a detail of the construction of the sealing gasket preferred for use in connection with the valve of the present invention.

FIG. 4 is an exploded view of the pump piston and its sheath.

In its preferred form the pump of the present invention comprises an inlet chamber 10 and an integral outlet chamber 11 preferably formed of three molded plastic sections: an upper generally hemispherical hollow section 12, a middle section 13, the upper portion of which is a hollow hemisphere adapted to fit in tight engagement with the upper hemisphere 12 and a lower section which is the upper part of a cylindrical outlet chamber; and a lower section 14 which completes the outlet chamber 11. The upper section 12 is formed with an integral inlet duct 15 which preferably extends downwardly to the end of the section or slightly beyond. The middle section has a hemispherical wall which, when affixed to the wall 12 of the upper section, forms the spherical inlet chamber 10 and is provided with an outlet port 16 which preferably extends downwardly to the level of the integral circular wall 37 which forms the upper portion of the outlet chamber 11. A discharge port 17 is formed in the lower end of the lower section 14. The inlet port 15 is of a size adapted to receive a supply tube 42 leading from a supply of material to be delivered to the patient, such as a bottle of saline solution, or the like, and the outlet 17 is likewise of a size adapted to engage a tube 43 for delivery of the pumped material to the patient.

The respective sections are connected together by means of a pair of interlocking lips, such as 32, on the interior wall of upper section 12 and the cooperating outer lip 33 on the outer wall of the hemispherical portion of section 13; and an inner lip 34 on the inner wall of the cylindrical portion 37 of the middle section 13, and lip 35 on the outer wall of section 14. The connections between the respective sections must be water and air-tight, and they must be strong enough to resist the pumping force applied to liquid within chamber 10 or to the weight of the liquid in the outlet chamber 11. This can readily be secured by cementing the respective lips 32, 33 and 34, 35 together, although the parts could be made to such accuracy that friction force alone would be sufficient to hold the parts together.

The interiors of the two chambers 10 and 11 are provided with a pair of parallel ribs, or bosses, such as 18 shown in FIG. 1 in the upper section 12; 19 and 20 in the hemispherical section of section 13 (shown in FIG. 2); and 22 (shown in FIG. 1) in the cylindrical portion of section 13, and 24 shown in the lower section 14. These bosses serve two purposes: (1) to properly align the various sections together, the device being properly assembled when boss 18 is aligned with boss 20 and the boss, or rib 22 is aligned with the boss, or rib, 24; and (2) they form the bearings for the float valves to be described hereafter. The bearings are formed by providing bearing slots, such as 26 shown in dotted lines in FIG. 1, in the lower pair of each set of ribs. Again, when the parallel ribs are properly aligned, the upper pair cooperates with the lower pair to form a cover for the bearing slots, so that the float valves cannot be displaced.

Each of the chambers 10 and 11 is provided with a float valve 50 cooperating respectively with the inlet 15 and the intermediate conduit, or duct, 16. Since these two float valves preferably are identical in construction, a description of one will be sufficient for both, and since they are identical in construction, the same reference characters can be applied to both float valves.

Preferably, the two float valves are held against extreme opening action by stops 38 and 39 which are formed in the bottom of the two chambers 10 and 11, as shown in FIG. 1. Such a limiting of movement of the float is desired to prevent any possibility of the float blocking the outlet from its chamber.

The valve of the present invention comprises a spherical float 50 preferably formed of two hollow hemispheres 51 and 52 tightly fitted together. A suitable connection between the two sections 51 and 52 can be formed by providing one section, such as 51, with an interior lip, not shown, and the other section, such as 52, with an outer lip, likewise not shown, which are slightly oversize and therefore must be forcibly inserted one within the other to form a water-tight seal. In this instance, any pressure exerted by fluid in the chamber 10 will be forcing toward the center of the float and therefore there is no danger of the two sections being forced apart from pressure of the fluid being pumped. It does, however, require a water-tight seal so that fluid will not leak into the interior of the float 50.

The float 50 is mounted on a lever arm 60, preferably formed integrally with the lower hemispherical section 52 as shown particularly in FIG. 1. The arm 60 is pivotally mounted within the chamber by means of a pivot shaft 61, the ends of which are reduced to provide suitable journals 62 and 63 (FIG. 2) adapted to be inserted in the bearing slots, such as 26 described above. In order to provide strength for the bearing shaft 61, it is preferred that a longitudinally extending rib 64 (FIG. 1) be formed integrally with the pivot shaft 61 and that the arm 60 be integral therewith. Even though the pump casing comprising chambers 10 and 11, and the valve element comprising the pivot shaft 61, lever arm 60 and lower hemisphere 52 of the float 50 are made of styrene, which has no self-lubricating properties, the assembly of the bearing notches 26 and the journals 62, 63 provide for easy movement of the valve within its pivot bearing as the liquid in the chambers provides very excellent lubrication. Hence, the float will be responsive to exceedingly small differences in the pressure within the chamber 10. It can be mentioned at this point that when the pump is in operation, both chambers are filled with the liquid being pumped. Both valves have a buoyancy which causes them to rise as far as possible toward the top of their respective chambers. When the piston 100 and its sheath 102 (to be described hereafter) are projected inwardly, the increase in pressure in chamber 10 forces the valve in chamber 11 open, and liquid will flow from chamber 10 into chamber 11. When movement of the piston stops, the valve in chamber 11 closes immediately. Then as the piston is withdrawn, it causes a negative pressure, or suction, in chamber 10, thereby causing the valve in that chamber to open and permitting the inflow of further liquid from the source of supply. Obviously, the size of the float 50 must be carefully calculated so that it will close inlet 15 with more force than will come from the height of liquid above it and small enough to be responsive to the suction caused by the withdrawal of the piston.

The lever arm 60 is provided at an intermediate point with a doughnut-shaped section 65 (FIG. 1) adapted to receive a sealing gasket 70 to be described in the next paragraph. Preferably, this doughnut-shaped section 65 will be located about one-third of the distance from the axis of the pivot shaft 61 to the center of the spherical float 50, whereby any lifting force on the float 50 will be multiplied by the ratio 3:1 to apply force from the gasket 70 against the lower end of the inlet 15 or 16, as the case may be. Obviously, this doughnut-shaped section 65 must be in alignment with the inlet valve 15.

The sealing gasket 70 is shown particularly in detail in FIG. 3. Preferably, it is made of a very light and very flexible silicone rubber of medically approved quality. It comprises a plate section 71 adapted to be at about the plane of the upper edge of the arm 60; a stem 72 adapted to fit tightly within the interior 66 of the doughnut-shaped section 65; and a conical section 74, connecting the plate 71 and stem 72. Preferably it has a smaller section 73 at the lower end of the stem 72. The smaller section 73 is desirable in that it makes it easy to start the gasket 70 into the hole 66 of the doughnut-shaped section 65, and then it can be used to pull the tightly fitting stem into the hole 66. The conical section 74 between the plate 71 and the stem 72 enables the plate to be removed slightly from arm 60, so that it can tilt easily in order to conform to the open end of its inlet port. Preferably, the gasket is formed of very resilient material so that it may readily be inserted in the lever arm 60 and so that the plate section 71 of the gasket will deform to fit tightly against any irregularities occurring in the lower end of the inlet 15 or 16 and to be tilted, if necessary, to form a tight-fitting seal with the inlet 15 or 16.

The pumping displacement, or force, of the present invention is secured by the inward and outward movement of a piston 100 shown in place in FIG. 1 and in an exploded view in FIG. 4. Associated with, and cooperating with, the piston 100 is a tightly fitting sheath 102. The piston and sheath extend into the inlet chamber 10 through an opening 108 in the upper portion of the upper section 12, so that movement of the piston 100 and sheath 102 inwardly toward the center of the inlet section applies a pumping force to liquid within that chamber, assuming that the chamber is full of liquid, as it should be to secure a pumping operation.

The open end of the sheath 102 is provided with an inwardly extending lip 103 which must be forced and deformed to receive the piston 100 as the piston 100 fits tightly within the body of the sheath 102. It is desired that there be no possibility for the entrapment of air between sheath 102 and piston 100, and the inwardly extending ear 103 provides a sealing ring for that purpose, which sealing ring is applied with some force to the piston as the sheath is extended. It will be noted in FIG. 4 that the cylindrical wall 104 of the sheath 102 is thinner than the end wall 105. This is done to prevent stretching of the sheath from occurring at the end of the piston, as that would tend to form a break in the sheath at the end of the piston. Thus, the sheath is stronger at the end where tension would normally be greater and the tension caused by stretching the sheath is transferred to the cylindrical wall 102. This has the advantage of not only preventing rupture of the sheath, but also provides greater force for the return of the piston to its outward and inactive position.

It is assumed in this application that the operating force will be applied to some drive member (not shown), such as a lever or rocker arm operated by a small electric motor. One such device called a pump actuator or driver is described in my copending application, filed Apr. 25, 1973, Ser. No. 354,242 now U.S. Pat. No. 3,798,982. The necessary action can be secured by pushing the piston inwardly and then releasing it, leaving the return force to the tension within the sheath 102, which preferably is formed of a resilient rubber-like material.

The sheath is also provided with an outwardly extending annular sealing ring section 106 adapted to fit into a depression 109 formed as an annular groove around the entrance 108 for the piston and sheath. When a cap member 107 is forced down upon the sealing section 106, as by cementing, the use of the threaded parts, or the like, the pressure deforms the sealing section 106 to form a completely air-tight seal between the sheath and the casing of the pump. As shown in FIGS. 1 and 4, it is preferred that the outer end 101 of the piston 100 be of reduced diameter so that the cap section 107 not only locks the sheath in place, but also holds the piston 100 from moving out of its proper position in the pump, the enlarged section of the piston 100 abutting the smaller aperture 110 at the outer end of the cap 107.

It perhaps should be mentioned that in its preferred form the sheath 102 should fit snugly on the piston 100 so that no air will be trapped between the two. Preferably, the sheath 102 is so proportioned that when the piston 100 and sheath 102 are inserted in the chamber 10, the shoulder between the piston 100 and its neck 101 will abut the inside of the outer end of the cap 107 and the sheath will be relaxed, i.e., not under tension, but still tightly fitting to the piston at all points. However, when the pump is placed in its operating position with respect to the pump driver, it is preferred that the piston be moved inwardly slightly so that at that time, but not before, there will be a little tension in the side wall of the sheath. What must be emphasized is that when a vacuum is created in the chamber 10 by the withdrawal of the piston, there must be no air between the piston and the sheath or the vacuum in the chamber might cause the sheath to bulge and thus make the pump inaccurate.

It should also be mentioned that in the assembly of the pump it is necessary to place a lubricant on the piston whereby the piston and the sheath can have a sliding contact with each other. It is well known that rubber has a relatively high coefficient of friction, and it is necessary to have as little friction as possible between the piston and the sheath so that the force from the tensioning of the cylindrical wall of the sheath will be sufficient to quickly force the piston to its most retracted position. I have found that a good grade of silicone lubricant is sufficient for this purpose.

It is believed tht operation of the pump will be readily understood. At the start, the two chambers 10 and 11 are completely filled with liquid to be pumped. This is readily secured by turning the pump from the upright position shown in FIG. 1 to a horizontal position at 90° thereof. When this is done, the float valves 50 become inoperative and both chambers fill completely with liquid from the source of supply, not shown, entering through tube 42. Then, when the pump is turned to the upright position, both chambers are full of liquid, and the valves are operative to close both inlets 15 and 16.

The pump is now ready for operation. The periodic application of force inwardly against the outer end of piston 100 causes the piston and sheath to penetrate into the liquid in chamber 10, thereby forcing the liquid through the intermediate duct 16 into the lower chamber 11. Normally, this chamber is closed by the buoyancy of the float 50 in that chamber. However, when the piston and its sheath are projected into chamber 10, the liquid in that chamber (being incompressible) must overcome the closing force of the float valve 50, 60, 70 in the lower chamber 11. When the piston 100 is retracted or withdrawn, the float valve in chamber 11 closes, as the forces secured from the float 50 in the chamber is greater than the weight of fluid in chamber 10. Then, as the piston and its sheath moves outwardly, it creates a suction, or negative liquid pressure, in chamber 10, and the float valve 50 into that chamber opens and lets further liquid come from the supply source through tube 42. By this means an adequate and very accurate flow of intravenous feeding liquid is secured. The amount of liquid delivered with any stroke of this piston is readily controlled by adjusting the length of the stroke, and the frequency of such delivery is secured by controlling the frequency of piston operation. Thus, the pump of the present invention is easily adjustable as to amount of material supplied with any pump stroke and the frequency of strokes is also readily controlled, as is clearly described in my copending application above mentioned.

In the event it is desired to disconnect the pump from its actuator (as when moving a patient from one room to another) and to use it as a "through-flow" device to avoid disconnecting the pump from its inlet and outlet tubes 42 and 43, it can readily be done by turning the pump upside down. In that position, both of the float valves are disabled as the floats lift the valve seals 70 away from the respective inlets. So long as the source of material is higher than the patient, the liquid will flow upwardly through the inlet 15 and thence through inlet 16, and thence to outlet 17 and tube 43. Thus the pump of the present invention, when once filled and connected to a patient through tube 43 to the patient, can be used as a pump or not used, without disconnecting the pump from either tube 42 or 43, or removing the needle from the patient.

It is believed obvious that since there is no rubbing contact between the piston or its sheath, and any part of the pump body, there is no danger of leakage or the material within the pump becoming polluted or unsterile. Also, the pump can be used for pumping blood as there is no rubbing contact which is destructive of blood cells. One further point that can be mentioned is that should air enter the pump through the tube 42, it can only form a bubble in the top of chamber 10 and cannot be pumped to the blood stream of the patient. Such a bubble can cause slight inaccuracies in the amount of liquid being pumped as air is readily compressed. In the event the air bubble were large, the pump would become inoperative as the air would compress sufficiently to completely balance the pumping force from the piston, but still no air would be pumped to the patient. Thus, the pump of the present invention is inherently a bubble trap as well.

It is obvious that many slight modifications can be made in the preferred form of the present invention, such as changing the shape of the chambers, although the spherical shape of the inlet and pumping chamber is highly preferable, the float valve can be of other construction, and the like. Accordingly, the claims should be given an interpretation commensurate with their wording.

What is claimed is:

1. A pump for the precise metering of liquids for delivery to a patient comprising:
    (a) a non-deformable inlet chamber having an inlet thereto and an outlet duct therefrom and means forming a flow passage in communication with the outlet duct and adapted to be connected to the patient;
    (b) a one-way valve cooperating with said inlet;
    (c) a substantially incompressible displacement piston having a first end portion always projecting inwardly through an opening in one wall of said inlet chamber and a second end portion which remains outside said inlet chamber, said second end portion always projecting outwardly through the opening in the wall and being adapted for engagement by piston means, said piston being adapted for reciprocating movement in a direction inwardly of the inlet chamber from a first retracted position to a second projected position and then outwardly to said first position, the movement of said piston from said first position to said second position causing the discharge of a precise quantity of liquid from said inlet chamber through said outlet duct and the return movement of said piston from said second position to said first position causing further liquid to be drawn into said inlet chamber through said inlet so that said inlet chamber remains filled with liquid; and
    (d) a flexible sheath of resilient material enclosing and in tight-fitting engagement with the entire portion of said piston which is inside said inlet chamber, a portion of said sheath being in air-tight engagement with the adjacent portion of said one wall of said inlet chamber in contact therewith and having sealing means for preventing the admission of air between said sheath and that portion of said piston enclosed by and in contact therewith, said sheath remaining in continuous contact with the entire portion of said piston which is inside the inlet chamber during movement of said piston between said first and second positions.

2. A pump for the precise metering of liquids for delivery to a patient comprising:
    (a) a non-deformable inlet chamber having an inlet thereto and an outlet duct therefrom;
    (b) a non-deformable outlet chamber in communication with said inlet chamber via said outlet duct from said inlet chamber, said outlet chamber having an outlet therefrom;
    (c) a one-way valve cooperating with said inlet to said inlet chamber;
    (d) a one-way valve cooperating with said outlet duct from said inlet chamber;
    (e) a single substantially incompressible displacement piston having a first end portion projecting inwardly through one wall of said inlet chamber and a second end portion which remains outside said inlet chamber, said second end portion being adapted for engagement by piston actuating means, said piston being adapted for reciprocating movement in a direction inwardly of the inlet chamber from a first retracted position to a second projected position and then outwardly to said first position, the movement of said piston from said first position to said second position causing the discharge of a precise quantity of liquid from said inlet chamber into said outlet chamber through said outlet duct and the discharge of a like amount of liquid from said outlet chamber through said outlet, and the return movement of said piston from said second position to said first position causing further liquid to be drawn into said inlet chamber through said inlet to keep the inlet chamber filled;

(f) a flexible sheath of resilient material enclosing and in air-tight engagement with the entire portion of said piston which is inside said inlet chamber, a portion of said sheath being in air-tight engagement with the adjacent portion of said one wall of said inlet chamber in contact therewith and having sealing means for preventing the admission of air between said sheath and that portion of said piston enclosed by and in contact therewith, said sheath remaining in continuous contact with the entire sheath enclosed portion of said piston which is inside the inlet chamber during movement of said piston between said first and second positions; and (g) means forming a flow passage in communication with the outlet duct and adapted to be connected to the patient.

3. A pump for the precise metering of liquids for delivery to a patient comprising;

(a) a non-deformable inlet chamber having an inlet thereto and an outlet duct therefrom;

(b) a one-way valve cooperating with said inlet;

(c) a single substantially incompressible displacement piston having a first end portion projecting inwardly through an opening in one wall of said inlet chamber and a second end portion which remains outside said inlet chamber, said second end portion being adapted for engagement by piston actuating means, said piston being adapted for reciprocating movement in a direction inwardly of the inlet chamber from a first retracted position to a second projected position and then outwardly to said first position, the movement of said piston from said first position to said second position causing the discharge of a precise quantity of liquid from said inlet chamber through said outlet duct and the return movement of said piston from said second position to said first position causing further liquid to be drawn into said inlet chamber through said inlet to keep said inlet chamber filled;

(d) a flexible sheath of resilient material enclosing and in air-tight engagement with the entire portion of said piston which is inside said inlet chamber, a portion of said sheath and the portion of the wall of said inlet chamber in contact therewith forming means to prevent admission of air to said inlet chamber, and said sheath being of such configuration as to prevent admission of air between said sheath and that portion of said piston enclosed by and in contact therewith, said sheath remaining in continuous contact with the entire portion of said piston which is inside the inlet chamber during movement of said piston between said first and second positions; and (e) means forming a flow passage in communication with the outlet duct and adapted to be connected to the patient.

4. A pump for the precise metering of liquids comprising:

(a) a non-deformable inlet chamber adapted to be completely filled with liquid having an inlet thereto and an outlet duct therefrom;

(b) a non-deformable outlet chamber adapted to be completely filled with liquid in communication with said inlet chamber via said outlet duct from said inlet chamber, said outlet chamber having an outlet therefrom;

(c) a one-way valve cooperating with said inlet to said inlet chamber;

(d) a one-way valve cooperating with said outlet duct from said inlet chamber;

(e) a single substantially incompressible displacement piston having a first end portion projecting inwardly through one wall of said inlet chamber and a second end portion which remains outside said inlet chamber, said second end portion being adapted for engagement by piston actuating means, said piston being adapted for reciprocating movement in a direction inwardly of the inlet chamber from a first retracted position to a second projected position and then outwardly to said first position, the movement of said piston from said first position to said second position causing the discharge of a precise quantity of liquid from said inlet chamber into said outlet chamber through said outlet duct and the discharge of a like amount of liquid from said outlet chamber through said outlet, and the return movement of said piston from said second position to said first position causing further liquid to be drawn into said inlet chamber through said inlet;

(f) a flexible sheath of resilient material enclosing and in air-tight engagement with the entire portion of said piston which is inside said inlet chamber, said sheath and the portion of the wall of said inlet chamber in contact therewith forming means to prevent admission of air to said inlet chamber, and said sheath being of such configuration as to prevent admission of air between said sheath and that portion of said piston enclosed by and in contact therewith, said sheath remaining in continuous contact with the entire portion of said piston which is inside the inlet chamber during movement of said piston between said first and second positions; and (g) means forming a flow passage in communication with said outlet duct and adapted to be connected to the patient.

5. In a precision disposable intravenous liquid delivery pump which is small in size for precision delivery of an intravenous liquid from a source to a patient for use with an actuator of a type having a movable member which is movable by the actuator, a housing formed essentially of plastic and having a chamber formed therein that is substantially inexpandable, said housing being formed with an inlet having an inlet flow passage therein in communication with said chamber and an outlet having an outlet flow passage therein in communication with said chamber, inlet valve means carried by the housing and movable between open and closed positions for controlling the flow of liquid through the inlet passage into said chamber, additional valve means mounted within the housing movable between open and closed positions for controlling the flow of intravenous liquid through the outlet passage from the chamber, means forming a flow passage communicating with the outlet flow passage and adapted to be connected to the patient, said housing when said pump is in use being disposed generally upright with the inlet flow passage communicating with the chamber at a level above the outlet flow passage, said housing having an upper portion forming an upper wall of the chamber, said upper wall having an opening therein, a piston-like means extending through said opening for a reciprocatory stroke-like movement between a first retracted position and a second projected position to displace liquid in the chamber, said chamber having a volume substantially greater than the volume displaced by said piston-like means when moved from its first retracted position to its second projected position whereby the volume of liquid displaced by stroke-like movement of the piston-like means from the first to the second position is substantially less than the volume of liquid in the chamber, the piston-like means including a reciprocatable rigid piston member extending through the opening in the upper wall and means forming a germ barrier-type seal between said piston member and said upper housing wall and permitting said reciprocatory motion of said piston member with respect to said housing, said piston member having a portion thereof remaining at all times outside of the chamber, said portion being adapted to be engaged by said movable member of said actuator for movement of said piston member between said first and second positions whereby when said chamber is filled with intravenous liquid and when said piston member is moved from said first position to said second position said additional valve means is moved to an open position and a precise quantity of intravenous liquid is caused to pass from the chamber through the outlet passage upon each such movement of the piston member and when said piston member is moved from said second position to said first position said additional valve means is moved to a closed position and said first-named valve means is moved to an open position and additional intravenous liquid is caused to flow from the source through the inlet passage into the chamber to keep the chamber filled so that the intravenous liquid supplied to the patient can be precisely ascertained by counting the number of strokes of said piston member, said pump being formed so that it is inexpensive and can be thrown away after use.

6. A pump as in claim 5 wherein said means forming a germ barrier type seal between the piston member and the housing also serves to yieldably return the piston-like member from the second position to the first position.

7. A pump as in claim 6 wherein said germ barrier means is flexible and made of resilient material that is stressed when the piston member is moved from its retracted to its projected position.

8. A pump as in claim 5 wherein said housing is constructed to form a substantially inexpandable outlet chamber, said outlet passage being in communication with said outlet chamber, and an additional outlet having a passage in communication with said outlet chamber, and wherein said additional valve member is disposed in the outlet chamber.

9. A pump as in claim 8 wherein a portion of said housing is circular in cross section and said piston member is aligned on an axis coincident with the central axis of the inlet chamber, said inlet chamber being circular in section.

10. A pump as in claim 9 wherein said inlet is offset from said axis and wherein said additional outlet is in alignment with said axis.

11. A pump as in claim 5 wherein said first named valve means includes a float valve member.

12. A pump as in claim 5 wherein said means forming a germ barrier type seal includes a flexible sheath made of resilient material enclosing the entire portion of said piston which is inside said chamber.

13. A pump as in claim 5 wherein said housing includes first and second parts and wherein said germ barrier type seal has an outer margin which is clamped between said first and second parts of said housing.

14. A pump as in claim 5 wherein said piston member has a substantially uniform cross-sectional area extending from the interior of the chamber to the exterior of the chamber.

15. A pump as in claim 5 together with yieldable means carried by the housing for yieldably urging said piston member from said second projected position to said first retracted position and cooperative means carried by the housing and the piston-like member for preventing the yieldable means from urging the piston-like member out of the housing.

16. A pump as in claim 5 wherein said upper wall is curved and serves to collect any bubbles of air which enter the inlet chamber to thereby prevent bubbles of air from being pumped into the patient.

17. In a precision disposable intravenous liquid delivery pump which is small in size for delivery of an intravenous liquid from a source of intravenous liquid to a patient for use with an actuator of a type having a movable member which is movable by the actuator, a housing formed essentially of plastic and having an inlet chamber and an outlet chamber formed therein, said housing being formed so that the inlet chamber and the outlet chamber are substantially inexpandable, said housing being formed with an inlet having an inlet flow passage therein in communication with said inlet chamber and an outlet for said inlet chamber having a flow passage establishing communication between said inlet chamber and said outlet chamber, said housing also being formed with an outlet for said outlet chamber having an outlet flow passage therein in communication with said outlet chamber and adapted to be connected to the patient, inlet valve means carried by said housing and movable between open and closed positions for controlling the flow of liquid through the inlet passage into said inlet chamber, outlet valve means within said housing movable between open and closed positions for controlling the flow of liquid through the flow passage extending between said inlet chamber and said outlet chamber, said housing when said pump is in use being disposed in a generally vertical direction with the inlet means of the inlet chamber being located above the outlet means of the inlet chamber, said housing having a wall forming the upper portion of the chamber, a single piston-like means including a piston member extending through an opening in said wall for reciprocatory stroke-like movement in a vertical direction between a first retracted position and a second projected position, said piston member being rigid and substantially incompressible and always having a portion thereof disposed in said inlet chamber and immersed in the liquid in said inlet chamber, said inlet chamber having a volume substantially greater than the volume occupied by the piston member in its second position whereby the volume of liquid displaced by stroke-like movement of the piston member from the first to the second position is substantially less than the volume of the liquid in the chamber, means forming a germ barrier-type seal between said piston member and said housing and permitting said reciprocatory movement of said piston member with respect to said housing, said piston member having a portion thereof remaining at all times outside of the inlet chamber, said portion being adapted to be engaged by said movable member of said actuator for movement of said piston member between said first and second positions whereby when said inlet and outlet chambers are filled with intravenous liquid and when said piston member moves from said first position to said second position, said outlet valve means is moved to an open position and a precise quantity of intravenous liquid is caused to pass from the inlet chamber through the outlet passage from the inlet chamber upon each stroke-like movement of the piston member and when said piston member is moved from said second position to said first positions, said outlet valve means is moved to a closed position and said first-named valve means is moved to an open position and additional intravenous liquid is caused to flow from the source through the inlet passage into the inlet chamber to keep the inlet chamber filled so that the intravenous liquid supplied to the patient can be precisely ascertained by counting the number of strokes of said piston member, said pump being formed so that it is inexpensive and can be thrown away after use.

18. In a precision intravenous liquid delivery pump assembly which is small in size for precision delivery of an intravenous liquid from a source to a patient, means forming a housing having a chamber formed therein adapted to be filled with a substantially incompressible liquid, and means for recurrently displacing liquid from the chamber and for delivering the same through an outlet passage to the patient, said chamber having one wall thereof provided with an opening, said means including a single piston member extending through said opening in said wall for reciprocatory stroke-like motion for movement between a first retracted position to cause liquid to be drawn into the chamber and a second projected position to displace liquid from the chamber, said piston member being rigid and substantially incompressible, said chamber having a volume substantially greater than the volume displaced by the piston member in its second position whereby the volume of the liquid displaced by the stroke-like movement of the piston member from the first to the second position is substantially less than the volume of liquid in the chamber, a flexible sheath formed of resilient material enclosing and in air-tight engagement with the portion of said piston member within the chamber, said sheath having a portion secured to said wall to thereby form a seal to prevent the admission of air into said chamber, said sheath being of such configuration and so dimensioned as to prevent admission of air between said sheath and the portion of the piston member in contact therewith, said sheath remaining in continuous contact with the entire portion of said piston member which is inside said chamber during movement of said piston member between said first and second positions.

19. An assembly as in claim 18 in which stressing of the sheath provides means for yieldably urging the piston-like member into its first retracted position.

20. An assembly as in claim 18 wherein the upper extremity of the sheath is provided with an inwardly extending lip frictionally engaging the surface of the piston member.

21. An assembly as in claim 18 together with a lubricant carried by the piston member to reduce the friction between the piston member and the sheath.

22. An assembly as in claim 21 wherein said sheath is formed of a rubber-like material and the lubricant is a silicon-type lubricant.

23. An assembly as in claim 18 wherein said piston member is disposed in a vertical position.

* * * * *

UNITED STATES PATENT AND TRADEMARK OFFICE
CERTIFICATE OF CORRECTION

PATENT NO. : 4,165,208

DATED : August 21, 1979

INVENTOR(S) : Ingemar Lundquist

It is certified that error appears in the above-identified patent and that said Letters Patent are hereby corrected as shown below:

In the Related U.S. Application Data:

Delete:
    Continuation of Ser. No. 704,540, Jul. 12, 1976, abandoned, which is a continuation of Ser. No. 431,753, Jan. 8, 1974, Pat. No. 3,874,826, which is a continuation-in-part of Ser. No. 329,425 Feb. 5, 1973, abandoned.

Insert:
    Continuation of Ser. No. 704,540, Jul. 12, 1976 abandoned, which is a continuation of Serial No. 556,549, filed March 10, 1975, which is a continuation of Ser. No. 431,753, Jan. 8, 1974, Pat. No. 3,874,826, which is a continuation-in-part of Ser. No. 329,425, Feb. 5, 1973, abandoned.

Signed and Sealed this

Ninth Day of February 1982

[SEAL]

Attest:

*Attesting Officer*

GERALD J. MOSSINGHOFF

*Commissioner of Patents and Trademarks*